(12) United States Patent
Nisato

(10) Patent No.: US 6,218,414 B1
(45) Date of Patent: *Apr. 17, 2001

(54) USE OF AN ANGIOTENSIN II ANTAGONIST AND A BENZOFURAN DERIVATIVE IN THE TREATMENT OF CARDIOVASCULAR COMPLAINTS

(75) Inventor: Dino Nisato, Saint Georges d'Orques (FR)

(73) Assignee: Sanofi, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/169,115

(22) Filed: Oct. 8, 1998

Related U.S. Application Data

(63) Continuation of application No. 08/663,450, filed on Jun. 13, 1996, now abandoned.

(30) Foreign Application Priority Data

Jun. 14, 1995 (FR) .................................. 95 07064

(51) Int. Cl.[7] ........................ A61K 31/41; A61K 31/34
(52) U.S. Cl. ................................... 514/382; 514/469
(58) Field of Search ...................... 514/469, 382

(56) References Cited

FOREIGN PATENT DOCUMENTS

| | | |
|---|---|---|
| 450 415 A1 | 4/1990 | (EP) . |
| 471 609 A1 | 2/1992 | (EP) . |
| WO 94/09778 | 5/1994 | (WO) . |
| WO 95/09625 | 4/1995 | (WO) . |

OTHER PUBLICATIONS

Ramahi T.M. et al., Cardiol Clinics, 1995, 13, 1, 5–26, "Medical Therapy and Prognosis in Chronic Hear Failure".

C. Cazaubon et al., J. Pharmacol. Exp. Ther., 1993, 265:2, 826–834, "Pharmacological Characterization of SR 47436, a New Nonpeptide $At_1$ Subtype Angiotensin II Receptor Antagonist".

Dickstein, K. et al., JACC, 1995, 26: 2, 438–445, "Comparison of the Effects of Losartan and Enalapril on Clinical Status and Exercise Performance in Patients with Moderate or Severe Chronic Heart Failure".

McMurray et al., Exp. Invest. Drugs, 1995, 4: 11, 1069–1090, "Ongoing and planned clinical trials in chronic heart failure and left ventricular dysfunction".

Mohacsi, P. et al., Praxis, 1996, 85: 8, 245–255, "Therapiebezogene Abklarung der Herzinsuffizienz in Klinik und Praxis".

*Primary Examiner*—Raymond Henley, III
(74) *Attorney, Agent, or Firm*—Bacon & Thomas

(57) ABSTRACT

The invention relates to the use of an angiotensin II antagonist and a benzofuran derivative with antiarrhythmic activity in the treatment of cardiovascular complaints, in particular in the treatment of cardiac insufficiency.

23 Claims, No Drawings

USE OF AN ANGIOTENSIN II ANTAGONIST AND A BENZOFURAN DERIVATIVE IN THE TREATMENT OF CARDIOVASCULAR COMPLAINTS

This is contunuation of U.S. application Ser. No. 08/663,450 filed Jun. 13, 1996, now abandoned.

The present invention relates to the combined use of an angiotensin II antagonist and a benzofuran derivative for the treatment of cardiovascular complaints, in particular the treatment of cardiac insufficiency.

The present invention relates more particularly to the use of irbesartan and amiodarone in the treatment of cardiovascular complaints, in particular in the treatment of cardiac insufficiency.

The present invention also relates to a novel pharmaceutical composition which is useful in particular for the treatment of cardiac insufficiency. This pharmaceutical composition consists of 2 active principles, one being a benzofuran derivative known for its antiarrhythmic activity, the other being an angiotensin II antagonist compound.

Cardiac insufficiency is defined as a pathological state associated with a decrease in the contractility of the myocardium and in which the heart is incapable of pumping the amount of blood required to satisfy the metabolic demand of various organs and tissues of the body.

According to the study by Framingham (P. A. McKee et al., New Engl. J. Med. 1971, 285, 1441–1446), it appears that cardiac insufficiency is not a disease in itself but a clinical manifestation of various heart disorders. Indeed, several forms of heart pathology may lead to ventricular dysfunction and cause the syndrome of cardiac insufficiency. Thus, with cardiac insufficiency being a sum of syndromes developing differently and having various etiologies, it is clear that a single therapeutic agent is not sufficient to treat it.

There is a strong relationship between left ventricular hypertrophy and sudden death, this relationship being partly explained by the combination of left ventricular hypertrophy and ventricular arrhythmia.

Patients suffering from severe cardiac insufficiency have a high level of ectopic ventricular activity and sudden death due to cardiac arrhythmias is the cause of more than 40% of deaths by cardiac insufficiency.

The high mortality rate in patients suffering from cardiac insufficiency has led to the search for new therapeutic agents enabling their lives to be prolonged.

The use of vasodilators appears justified for the treatment of cardiac insufficiency. Furthermore, an improvement in the hemodynamics and in the neuroendocrine profile are obtained by a prolonged treatment with digitalis-like compounds, glycosides and/or diuretics and vasodilators.

An improvement in the treatment of cardiac insufficiency can also be expected using an inhibitor of the conversion enzyme alone or in combination with other therapeutic agents.

The results of the CONSENSUS I study (N. Engl. J. Med., 1992, 327, 678–684), of the SAVE study (N. Engl. J. Med., 1992, 327, 669–677) and of SOLVD (N. Engl. J. Med., 1991, 325, 293–302) show clearly that conversion enzyme inhibitors can be used to treat patients suffering from mild, moderate or serious cardiac insufficiency associated with left ventricular systolic dysfunctions. In this case, conversion enzyme inhibitors improve the quality of life and survival of the patients.

Currently, irrespective of the origin of the cardiac insufficiency, patients are treated in most cases with a combination of several medicinal products: digitalis-like compounds, diuretics and conversion enzyme inhibitors (J. G. F. Cleland et al., Br. Heart J., 1994, 72 (2, suppl.) 573–579).

International patent application Wo 93/20839 describes the long-term use of an inhibitor of the renin-angiotensin system, such as a conversion enzyme inhibitor, a renin inhibitor or an angiotensin II antagonist, in order to reduce the mortality after myocardial infarction. According to this invention, the inhibitor of the renin-angiotensin system may be administered in combination with another active principle such as a beta-adrenergic blocker, an anticoagulant or aspirin.

Canadian patent application 2,070,085 describes a sustained-release pharmaceutical composition which is useful for the treatment of hypertension, cardiac insufficiency and other coronary problems, comprising a calcium-channel blocker and a conversion enzyme inhibitor.

The beneficial action of losartan, an angiotensin II inhibitor, on patients suffering from cardiac insufficiency is shown in J. Hypertension, 1994, 12 (suppl. 2), p. S31–S35.

U.S. Pat. No. 4,868,179 claims a method for reducing the mortality associated with chronic cardiac insufficiency, comprising the oral administration of a pharmaceutical composition comprising hydralazine and isosorbide dinitrate.

European patent 0,527,720 describes a method of treating cardiac insufficiency by administration of a pharmaceutical composition comprising a conversion enzyme inhibitor and 7-fluoro-1-methyl-3-methylsulfinyl-4-quinolone.

International patent application WO 90/09171 describes cardioprotective medicinal preparations which are useful in coronary insufficiency and in the prevention of the occurrence of an infarction or sudden death, comprising amiodarone, a nitro derivative and, optionally, a beta-blocker.

The expression benzofuran derivative with antiarrhythmic activity is understood to refer to a compound such as that described in one of the following documents: U.S. Pat. No. 3,248,401 and 5,223,510, European patent 338,746 and patent applications Wo 88/07996, WO 89/02892, WO 90/2743 and WO 94/29289.

Among these compounds, amiodarone described in U.S. Pat. No. 3,248,401 and N,N-dibutyl-3-[4-((2-butyl-5-methylsulfonamido)benzofuran-3-ylcarbonyl)phenoxy]-propylamine or dronedarone, also known as SR 33589, and the salts thereof described in U.S. Pat. No. 5,223,510 are preferred.

The active metabolites of these compounds are also preferred compounds, in particular N-desethylamiodarone and the salts thereof described in French patent 2,550,091 and N-butyl-3-[4-(2-butyl-5-methylsulfonamido)benzofuran-3-ylcarbonyl)phenoxy]propylamine and the salts thereof described in U.S. Pat. No. 5,223,510.

Amiodarone is considered to be a class III antiarrhythmic agent (B. N. Singh et al., Current Opinion in Cardiology, 1994, 9, 12–22). It is used worldwide to treat ventricular and supraventricular arrhythmias.

Furthermore, preliminary studies relating to the prophylactic use of amiodarone in patients suffering from cardiac insufficiency, non-sustained ventricular tachycardia or these 2 syndromes give promising results.

Indeed, the GESICA study (H. C. Doval et al., Lancet, 1994, 344, 493–498) describes observations made on patients suffering from serious cardiac insufficiency, who were monitored for 2 years. This study shows that the treatment with amiodarone at low dose decreases the mortality and hospitalizations in all the subgroups examined and independently of a possible non-sustained ventricular tachycardia.

Another study (J. J. Mahmaria et al., Am. J. Cardiol. 1994, 74, 681–686) conducted on patients exhibiting a fraction of left ventricular ejection of less than 40% shows that amiodarone administered at daily doses of 50 to 100 mg improves the heart hemodynamics and contractility.

In patients exhibiting severe arrhythmia following a congestive cardiomyopathy, amiodarone constitutes a treatment of choice, in combination with conversion enzyme inhibitors, digitalis-like compounds or diuretics (Acta Med. Austriaca, 1992, 19 (3), 83–87).

Patent application WO 95/09625 describes the use of amiodarone in the treatment of cardiac insufficiency; in this case, amiodarone can be combined with another therapeutic agent such as, for example, a diuretic, a cardiotonic, a vasodilator or a conversion enzyme inhibitor.

Thus, the combination of an angiotensin II antagonist with amiodarone has never been envisaged hitherto for the treatment of cardiovascular complaints.

According to the present invention, the term angiotensin II antagonist is understood to refer to nonpeptide compounds which have a strong affinity for the receptors of angiotensin II of the subtype AT1: (M. I. Steinberg et al., Cardiovascular Drug Reviews, 1993, 11(3), 312–358). This generally concerns nitrogen-containing heterocycles substituted with a biphenylmethyl group itself bearing an acid group. Among the nitrogen-containing heterocycles which may be mentioned in particular are imidazoles and other 5-membered rings such as pyrroles, pyrazoles, isoxazoles, isothiazoles and triazoles. Such compounds are described in the following patents or patent applications: EP 28,834-A, EP 253, 310-A, EP 324,377-A, WO 91/14679, EP 392,317-A, EP 403,159-A, EP 573,271-A, WO 94/08989, WO 94/08990, U.S. Pat. No. 4,576,958, U.S. Pat. No. 4,582,847, U.S. Pat. No. 4,207,324 and U.S. Pat. No. 4,340,598.

Other angiotensin II inhibitor compounds are described in patents or patent applications relating to derivatives formed on condensed heterocycles, in particular benzimidazoles and imidazopyridines: EP 399,731-A, EP 400,974-A, EP 392,317-A, EP 260,613-A, EP 412,848-A, EP 420,237-A, EP 502,314-A, EP 503,162-A, EP 552,765-A, EP 546, 358-A, EP 595,151-A, EP 598,702-A, EP 245,637-A, U.S. Pat. No. 4,880,804, WO 93/190067, WO 94/01436 and WO 94/204,498.

Moreover, other angiotensin II inhibitor compounds are formed from optionally condensed 6-membered nitrogen-containing heterocycles. Such compounds are described in particular in the following patents or patent applications: EP 412,848-A, GB 2,234,748-A, WO 91/07404, EP 487,252-A, EP 443,983-A, EP 403,159-A, EP 434,249-A, EP 500,409-A, WO 94/03449, WO 94/07492, WO 94/11379, WO 94/11369 and WO 95/002596.

Finally, other types of structure have been described for angiotensin II inhibitor compounds, in particular in the following patents or patent applications: EP 566,060-A, WO 94/00450 and EP 604,259.

In particular, among the angiotensin II antagonists which are suitable for their use according to the invention and in the pharmaceutical compositions according to the invention, mention may be made of the following compounds; these compounds are known by their international non proprietary name or by their code name, the chemical structure associated with each code being shown below or described in Chemical Abstracts:

Irbesartan, losartan, valsartan, zolasartan, telmisartan,
A-81282: 4-(N-butyl-N-[(2'-[1H-tetrazol-5-yl]-biphenyl-4-yl)methyl]amino)pyrimidine-5-carboxylic acid,
A-81988: 2-[N-propyl-N-[2'-(1H-tetrazol-5-yl)biphenyl-4-ylmethyl]amino]pyridine-3-carboxylic acid,
ANA-756 or tasosartan,
BMS-184,698: methyl 2-cyclopropyl-3-[(2'-(1H-tetrazol-5-yl)[1,1'-biphenyl]-4-yl]oxy]-(5-methyl-2- oxo-1,3-dioxol-4-yl)quinoline carboxylate,
CGP-49870: 1-[[N-(1-oxopentyl)-N-[2'-(1H-tetrazol-5-yl)][1,1'-biphenyl]-4-yl]methyl]amino]methyl] cyclopentanecarboxylic acid,
CI-996: 2-propyl-4-[(3-trifluoroacetyl)pyrrol-1 1-yl]-1-[[2'-(1H-tetrazol-5-yl)[1,1-biphenyl]-4-yl]-methyl]-1H-imidazole-5-carboxylic acid,
CL-329,167: 2-butyl-6-(1-methoxy-1-methyl-ethyl)-3-[[2'-(1H-tetrazol-5-yl)[1,1'-biphenyl]-4-yl]-methyl]-4 (3H)-quinazolinone,
CP-161418: 2-butyl-4-chloro-1-(5-(2-(1H-tetrazol-5-yl) phenyl)pyrimidin-2-ylmethyl)imidazole-5-carboxylic acid,
D-8731: 2-ethyl-4-[[2'-(1H-tetrazol-5-yl)[1,1'-biphenyl]-4-yl]methoxy]quinoline,
DMP-581: 4-ethyl-2-propyl-1-[[2'-1H-tetrazol-5-yl)[1,1'-biphenyl]-4-yl]methyl]-1H-imidazole-5-carboxaldehyde,
DMP-811: 4-ethyl-2-propyl-1-[[2'-(1H-tetrazol-5-yl)[1, 1'-biphenyl]-4-yl]methyl]1H-imidazole-5-carboxylic acid,
DUP-532: 4-(pentafluoroethyl)-2-propyl-1-[[2'-(1H-tetrazol-5-yl)[1,1'-biphenyl]-4-yl]methyl]-1H-imidazole-5-carboxylic acid,
E-4177: 4'-[(2-cyclopropyl-7-methyl-3H-imidazo[4,5-b] pyrid-3-yl)methyl]-[1,1'-biphenyl]-2-carboxylic acid,
EMD-66397: potassium salt of ethyl 2-(2-butyl-4,5-dihydro-4-oxo-3-(2'-(1H-tetrazol-5-yl)-4-biphenylmethyl)-3H-imidazo(4,5-c)pyridine-5-ylmethyl)benzoate,
EXP-408: methyl 4-ethyl-1-(3-fluoro-2'-(3-methylbutoxycarbonylaminosulfonyl)biphenyl-4-ylmethyl)-2-propylimidazole-5-carboxylate,
EXP-970,
EXP-3174: 2-butyl-4-chloro-1-[(2'-(1H-tetrazol-5-yl)(1, 1'-biphenyl)-4-yl)methyl-1H-imidazole-5-carboxylic acid,
EXP-3892: 2-propyl-1-[[2'-(1H-tetrazol-5-yl)-[1,1'-biphenyl]-4-yl]methyl]-4-(trifluoromethyl)-1H-imidazole-5-carboxylic acid,
EXP-6803: sodium 2-[4-[2-n-butyl-4-chloro-5-(methoxycarbonylmethyl)-1-imidazolylmethyl] phenylaminocarbonyl]benzoate,
EXP-7711: 4'-[2-butyl-4-chloro-5-(hydroxymethyl) imidazol-1-ylmethyl]-1,1'-biphenyl-2-carboxylic acid,
GA-0050: sodium 2-(6-((2-ethyl-5,7-dimethyl-3H-imidazo(4,5-b)pyrid-3-yl)methyl)quinolin-2-yl) benzoate,
GR-138,950: 1-((3-bromo-2-(2-(((trifluoromethyl) sulfonyl)amino)phenyl)-5-benzofuranyl)methyl)-4-cyclopropyl-2-ethyl-1H-imidazole-5-carboxamide,
HN-65,021: 1-[(ethoxycarbonyl)oxy]ethyl 2-butyl-4-chloro-1-[[2'-(1H-tetrazol-5-yl)[1,1'-biphenyl]-4-yl] methyl]-1H-imidazole-5-carboxylate,
KT-3671: 5,6,7,8-tetrahydro-2-propyl-3-[[2'-(1H-tetrazol-5-yl)[1,1'-biphenyl]-4-yl]methyl]-4(3H)-cycloheptimidazolone,
KW-3433: 2-(2-ethyl-5,7-dimethyl-3H-imidazo(4,5-b) pyrid-3-ylmethyl)-5-(2H-tetrazol-5-ylmethyl)-10,11-dihydro-5H-dibenz(b,f)azepine,
L-158,809: 5,7-dimethyl-2-ethyl-3-((2'-(1H-tetrazol-5-yl) (1,1'-biphenyl)-4-yl)methyl)-3H-imidazo(4,5)pyridine monohydrate,
L-158,978: 2-ethyl-7-methyl-3-[2'-(tetrazol-5-yl) biphenyl-4-ylmethyl]-3H-imidazol[4,5-b]pyridine-5-carboxylic acid,
L-159,282,
L-159,686: 1,4-bis(N,N-diphenylcarbamoyl)piperazine-2 (S)-carboxylic acid,
L-159,689: N-[3,4-dihydro-4-oxo-2-propyl-3-[[2'-(1H-tetrazol-5-yl)([1,1'-biphenyl]-4-yl]methyl]-6-quinazolinyl]-N-pentylbenzamide, L-159,874: 1-(N,N-bis(3-chlorophenyl)carbamoyl)-4-(N, N-dipentylcarbamoyl)piperazine-2(S)-carboxylic acid, L-161,177: 2-ethyl-5,7-dimethyl-3-[[2'-(3H-1,2,3,5-oxathiadiazol-4-yl)[1,1'-biphenyl]-4-yl]-methyl]-S-oxido-3H-imidazo[4,5-b]pyridine, L-161,816: potassium salt of methyl 3-(3,5-dibromo-4-hydroxybenzyl)-7-methyl-2-propyl-3H-imidazo[4,5-b]piperidine-5-carboxylate,

L-162,154,

L-162,234: 1,1-dimethylethyl 2-(4'-(1-(3-(5-butyl)-2-oxo-2-(2-triflylphenyl)-(1,3,4-triazolyl)methyl)biphenyl)sulfonylaminocarboxylate, L-162,441: butyl [[4'-[[2-butyl-5-methyl-6-[(1-oxopentyl)amino]-3H-imidazo[4,5-b]pyrid-3-yl]-methyl][1,1'-biphenyl]-2-yl]sulfonyl]carbamate, L-163,007: N-(4'-(3-butyl-5-oxo-1-(5-propionamido-2-(trifluoromethyl)phenyl)-4,5-dihydro-1H-1,2,4-triazol-4-ylmethyl)biphenyl-2-ylsulfonyl)carbamic acid, L-163,017: butyl [[4'-[[6-(benzoylamino)-7-methyl-2-propyl-3H-imidazo[[4'5-b]pyrid-3-yl]-methyl][1,1'-biphenyl]-2-yl]sulfonyl]-3-methylcarbamate, LF-7–0156: 2-[[[2-butyl-1-[(4-carboxyphenyl)methyl]-1H-imidazol-5-yl]methyl]amino]benzoic acid, LR-B-081: methyl 2-((4-butyl-2-methyl-6-oxo-((2'-(1H-tetrazol-5-yl)-(1,1'-biphenyl)-4-yl)-methyl)-1-(6H)-pyrimidinyl)methyl)-3-thiophenecarboxylate, LY-285,434: 2-(5-(2-(2H-tetrazol-5-yl)phenyl)-1H-indol-1-yl)octanoic acid, ME-3221: 3-methoxy-2,6-dimethyl-4-[[2'-(1H-tetrazol-5-yl)[1-biphenyl]-4-yl]methoxy]pyridine, MK-996: N-[[4'-[(2-ethyl-5,7-dimethyl-3H-imidazo[4,5-b]pyrid-3-yl)methyl][1,1'-biphenyl]-2-yl]sulfonyl]benzamide, PD-123,177: 1-[(4-amino-3-methylphenyl)methyl]-5-(diphenylacetyl)-4,5,6,7-tetrahydro-1H-imidazo-[4,5-c]pyridine-6-carboxylic acid, PD-123,319: 1-[4-(dimethylamino)-3-methylbenzyl]-5-(diphenylacetyl)-4,5,6,7-tetrahydro-1H-imidazo[4,5-c]pyridine-6(S)-carboxylic acid, PD-150,304: 4-(2-butyl-5-(1-butyl-3-(5-methylthiophen-3-ylmethyl)-2,5-dioxoimidazolidin-4-ylidenemethyl)imidazol-1-ylmethyl)benzoic acid,

RWJ-38970,

RWJ-46458: ethyl [4-ethyl-4-methyl-6-oxo-1-[[2'-(1H-tetrazol-5-yl)[1,1'-biphenyl]-4-yl)methyl]-2-piperidinylidene]acetate, SC-48742: [1,1'-biphenyl]-2-carboxylic acid, 4'-[[2-butyl-4-chloro-5-(hydroxymethyl)-1H-imidazol-1-yl]methyl], SC-50560: 5-[4'-(3,5-dibutyl-1,2,4-triazol-1-ylmethyl)biphenyl-2-yl]-1H-tetrazole, SC-51316: 2,5-dibutyl-4-[2'-(1H-tetrazol-5-yl)biphenyl-4-ylmethyl]-3,4-dihydro-2H-1,2,4-triazol-3-one, SC-51895: 1,4-dibutyl-3-[2'-(1H-tetrazol-5-yl)biphenyl-4-ylmethyl]-2,3-dihydro-1H-imidazolin-2-one, SC-52458 or forasartan: 5-[(3,5-dibutyl-1H-1,2,4-triazol-1-yl)methyl]-2-[2-(1H-tetrazol-5-yl)phenyl]pyridine, SKF-108,566 or eprosartan, SL-910,102: 6-butyl-(2-phenylethyl)-5-((2'-(1H-tetrazol-5-yl)(1,1'-biphenyl)-4-yl)methyl-4(1H)pyrimidinone, TAK-536: 2-ethoxy-1-((2'-(5-oxo-2,5-dihydro-1,2,4-oxadiazol-3-yl)biphenyl-4-yl)methyl)1H-benzimidazole-7-carboxylic acid, TCV-116 or candesartan, U-96,849: 5,8-ethano-5,8-dimethyl-2-n-propyl-5,6,7,8-tetrahydro-1-[[2'-(1H-tetrazol-5-yl)(1,1'-biphenyl)-4-yl]methyl]-1H,4H-1,3,4a,8a, tetraazacyclopentanaphthalene-9-one, UP-269-6: 5-methyl-7-propyl-8-((2'-(1H-tetrazol-5-yl)biphenyl-4-yl)methyl)-1,2,4-triazolo(1,5-c)pyrimidin-2(3H)-one, UP-27,522: 7-butyl-5-hydroxy-6-(2'-(1H-tetrazol-5-yl)biphenyl-4-ylmethyl)-1,2,4-triazolo(1,5-a)pyrimidine,

UR-7198,

WAY-126,227: 5,6,7,8-tetrahydro-N-[2'-(1H-tetrazol-5-yl)[1,1'-biphenyl]-4-yl]methyl]-2-(trifluoromethyl)-4-quinazolinamine, WK-1492: dipotassium 2-(5-ethyl-3-(2-(1H-tetrazol-5-yl)biphenyl-4-yl)methyl-1,3,4-thiazolin-2-ylidene)aminocarbonyl-1-cyclopentenecarboxylate, XH-148: 2-propyl-4-(4-(2-pyridyl)piperazin-1-ylmethyl)-1-(2'-(1H-tetrazol-5-yl)biphenyl-4-ylmethyl)imidazole-5-carboxylic acid, XR-510: potassium salt of 1-((2' ((isopentyloxycarbonylamino)sulfonyl)-3-fluoro-(1,1'-biphenyl)-4-yl)methyl)-5-[2-(N-butyryl-N-pyrid-3-ylamino)propionyl]4-ethyl-2-propyl-1H-imidazole, YM-358: 2,7-diethyl-5-[[2'-(1H-tetrazol-5-yl)-[1,1'-biphenyl]-4-yl]methyl]-5H-pyrazolo[1,5-b][1,2,4]triazole, YM-31,472: 1-(ethoxycarbonyloxy)ethyl 2-butyl-4-(3,N-dimethyl-2-butenamido)-1-(2'-(1H-tetrazol-5-yl)biphenyl-4-ylmethyl)imidazole-5-carboxylate, irbesartan being particularly preferred, either as it is or in polymorphic form, or in the form of one of the salts or solvates thereof.

According to the present invention, it has now been found that the use of an angiotensin II antagonist and a benzofuran derivative with antiarrhythmic activity is reflected by a synergism of the effects in the treatment of cardiovascular complaints, in particular in the treatment of acute or chronic cardiac insufficiency.

More particularly, the use of an angiotensin II antagonist and amiodarone or dronedarone and the salts thereof or one of the active metabolites thereof is reflected by a synergism of the effects in the treatment of acute or chronic cardiac insufficiency, thereby making it possible to increase the patient survival rate and to decrease the mortality.

Thus, the subject of the present invention is the use of an angiotensin II antagonist and a benzofuran derivative with antiarrhythmic activity for the preparation of a pharmaceutical composition which is useful in the treatment of cardiovascular complaints, in particular in the treatment of acute or chronic cardiac insufficiency. More particularly, the subject of the present invention is the use of an angiotensin II antagonist and amiodarone or dronedarone, and the salts thereof or one of the active metabolites thereof as mentioned above, for the preparation of a pharmaceutical composition which is useful in particular in the treatment of acute or chronic cardiac insufficiency.

A preferred angiotensin II antagonist for the said use is irbesartan.

According to the present invention, the combination with an angiotensin II inhibitor may make it possible to decrease the dose administered of benzofuran derivative with antiarrhythmic activity. Thus, advantageously, the undesirable effects of amiodarone may be appreciably reduced.

During administration of the combination according to the invention (angiotensin II antagonist and benzofuran derivative) to the patient, any other useful medicinal product, for example such as a digitalis-like compound or a diuretic, may be administered simultaneously.

The subject of the present invention is also a novel pharmaceutical composition which comprises a benzofuran derivative with antiarrhythmic activity and an angiotensin II inhibitor compound with a pharmaceutical excipient. In particular, the subject of the invention is a novel composition for the treatment of cardiovascular complaints, in particular cardiac insufficiency, which comprises a benzofuran derivative with antiarrhythmic activity and an angiotensin II inhibitor compound with a pharmaceutical excipient.

More particularly, such a composition comprises:

amiodarone and an angiotensin II inhibitor, preferably irbesartan, with a pharmaceutical excipient, or alternatively:

dronedarone or one of the salts thereof and an angiotensin II inhibitor, preferably irbesartan, with a pharmaceutical excipient, or alternatively:

N-desethylamiodarone and an angiotensin II inhibitor, preferably irbesartan, with a pharmaceutical excipient, N-butyl-3-[4-((2-butyl-5-methylsulfonamido)-benzofuran-3-ylcarbonyl)phenoxy]propylamine and an angiotensin II inhibitor, preferably irbesartan, with a pharmaceutical excipient.

The composition is preferably one comprising:

10 mg to 600 mg of benzofuran derivative having antiarrhythmic activity and 1 mg to 500 mg of angiotensiln II inhibitor compound.

More particularly, this composition comprises:

50 mg to 400 mg of amiodarone and 20 mg to 200 mg of irbesartan or alternatively:

50 mg to 400 mg of N,N-dibutyl-3-[4-((2-butyl-5-methylsulfonamido)benzofuran-3-ylcarbonyl)phenoxy]-propylamine and 20 mg to 200 mg of irbesartan.

The pharmaceutical composition according to the invention may be administered 1 to 5 times a day, preferably 1 to 2 times a day, and better still once a day.

Such a composition is obtained by mixture with pharmaceutically suitable excipients in order to obtain a composition for oral, parenteral, nasal, inhaled, topical, transcutaneous or rectal administration, oral administration being preferred. Thus, tablets, capsules, granules, powders, solutions or suspensions may be prepared.

According to another aspect of the invention, the angiotensin II antagonist and the benzofuran derivative with antiarrhythmic activity mentioned above may be administered sequentially for the treatment of cardiovascular complaints, in particular cardiac insufficiency.

The invention thus also relates to a kit for the treatment of cardiovascular complaints, in particular for the treatment of acute or chronic cardiac insufficiency by sequential administration of an angiotensin II antagonist and a benzofuran derivative with antiarrhythmic activity, wherein the said angiotensin II antagonist and the said benzofuran derivative are in separate packaging. More particularly, the said kit contains an angiotensin II antagonist, in particular irbesartan, and amiodarone, or dronedarone or one of the salts thereof, or one of the active metabolites thereof as mentioned above.

The invention further relates to a method of treating cardiovascular complaints in particular acute or chronic cardiac insufficiency, which comprises administering an effective amount of an angiotensin II antagonist and a benzofuran derivative with antiarrhythmic activity.

In particular, said method comprises administering an angiotensin II antagonist and amiodarone or N,N-dibutyl-3-[4-((2-butyl-5-methylsulfonamido)benzofuran-3-ylcarbonyl)phenoxy] propylamine or one of the salts thereof or N-desethylamiodarone or N-butyl-3-[4-((2-butyl-5-methylsulfonamido)benzofuran-3-ylcarbonyl)phenoxy] propylamine.

Advantageously, the angiotensin II antagonist which is administered is irbesartan.

The examples which follow illustrate the invention.

EXAMPLE 1

Tablet

| | |
|---|---|
| Amiodarone hydrochloride | 150 mg |
| Irbesartan | 25 mg |
| Lactose | 48.5 mg |
| Cornstarch | 44 mg |
| Talc | 25 mg |
| Polyvinylpyrrolidone | 9 mg |
| Anhydrous colloidal silica | 0.5 mg |
| Magnesium stearate | 3.0 mg |
| Purified water qs | 300 mg |

EXAMPLE 2

Tablet

| | |
|---|---|
| Amiodarone hydrochloride | 200 mg |
| Irbesartan | 50 mg |
| Lactose | 72.5 mg |
| Modified cornstarch | 48 mg |
| Talc | 25 mg |
| Anhydrous colloidal silica | 0.5 mg |
| Magnesium stearate | 4.0 mg |
| | 400 mg |

EXAMPLE 3

I. v. Injectable Solution

| | |
|---|---|
| Amiodarone hydrochloride | 200 mg |
| Irbesartan | 25 mg |
| Polysorbate 80 | 500 mg |
| Benzyl alcohol | 100 mg |
| Water for injectable preparation qs | 5 ml |

EXAMPLE 4

Tablet

| | |
|---|---|
| Dronedarone | 150 mg |
| Irbesartan | 25 mg |
| Lactose | 47.5 mg |
| Cornstarch | 40 mg |
| Talc | 25 mg |
| Hydroxypropylmethylcellulose | 9 mg |

| -continued | |
|---|---|
| Anhydrous colloidal silica | 0.5 mg |
| Magnesium stearate | 3.0 mg |
| Purified water qs | 300 mg |

EXAMPLE 5

Tablet

| Amiodarone hydrochloride | 150 mg |
|---|---|
| Angiotensin II inhibitor | 50 mg |
| Lactose | 52.5 mg |
| Cornstarch | 20 mg |
| Talc | 15 mg |
| Polyvinylpyrrolidone | 9 mg |
| Anhydrous colloidal silica | 0.5 mg |
| Magnesium stearate | 3.0 mg |
| Purified water qs | 300 mg |

EXAMPLE 6

Tablet

| Amiodarone hydrochloride | 100 mg |
|---|---|
| Angiotensin II inhibitor | 25 mg |
| Lactose | 128.5 mg |
| Modified cornstarch | 50 mg |
| Talc | 25 mg |
| Anhydrous colloidal silica | 0.5 mg |
| Magnesium stearate | 1.0 mg |
| Purified water qs | 400 mg |

What is claimed is:

1. A method of treating cardiovascular complaints, which comprises administering an effective amount of an angiotensin II antagonist and a benzofuran derivative with antiarrhythmic activity.

2. The method as claimed in claim 1, wherein the cardiovascular complaints are acute or chronic cardiac insufficiency.

3. The method as claimed in claim 1, which comprises administering an angiotensin II antagonist and amiodarone or N,N-dibutyl-3-[4-((2-butyl-5-methylsulfonamido) benzofuran-3-ylcarbonyl) phenoxy]propylamine or one of the salts thereof or N-desethylamiodarone or N-butyl-3-[4-((2-butyl-5-methylsulfonamido)benzofuran-3-yl-carbonyl) phenoxy]propylamine.

4. The method as claimed in claim 1, in which the angiotensin II antagonist is irbesartan.

5. A pharmaceutical composition which comprises a benzofuran derivative with antiarrhythmic activity and an angiotensin II inhibitor compound with a pharmaceutical excipient.

6. The pharmaceutical composition as claimed in claim 5, comprising amiodarone and an angiotensin II inhibitor, with a pharmaceutical excipient.

7. The pharmaceutical composition as claimed in claim 5, comprising N,N-dibutyl-3-[4-((2-butyl-5-methylsulfonamido)benzofuran-3-ylcarbonyl)phenoxy] propylamine or one of the salts thereof and an angiotensin II inhibitor, with a pharmaceutical excipient.

8. The pharmaceutical composition as claimed in claim 5, comprising N-desethylamiodarone and an angiotensin II inhibitor, with a pharmaceutical excipient.

9. The pharmaceutical composition as claimed in claim 5, comprising N-butyl-3-[4-((2-butyl-5-methylsulfonamido) benzofuran-3-ylcarbonyl)phenoxy]propylamine and an angiotensin II inhibitor, with a pharmaceutical excipient.

10. The pharmaceutical composition as claimed in claim 6, in which the angiotensin II inhibitor is irbesartan.

11. The pharmaceutical composition as claimed in claim 5, comprising 10 mg to 600 mg of benzofuran derivative with antiarrhythmic activity and 1 mg to 600 mg of angiotensin II inhibitor compound.

12. The pharmaceutical composition as claimed in claim 5, comprising 50 mg to 400 mg of amiodarone and 20 mg to 200 mg of irbesartan.

13. The pharmaceutical composition as claimed in claim 5, comprising 50 mg to 400 mg of N,N-dibutyl-3-[4-((2-butyl-5-methylsulfonamido)benzofuran-3-ylcarbonyl) phenoxy)propyl amine and 20 mg to 200 mg of irbesartan.

14. The pharmaceutical composition as claimed in claim 5, for oral administration.

15. A method for the treatment of cardiovascular complaints comprising administering the pharmaceutical composition as claimed in claim 5.

16. A method for the treatment of acute or chronic cardiac insufficiency comprising administering the pharmaceutical composition as claimed in claim 5.

17. A kit for the treatment of cardiovascular complaints, in particular for the treatment of acute or chronic cardiac insufficiency by sequential administration of an angiotensin II antagonist and a benzofuran derivative with antiarrhythmic activity, wherein the said angiotensin II antagonist and the said benzofuran derivative are packaged separately.

18. The kit as claimed in claim 17, wherein the angiotensin II antagonist is irbesartan.

19. The kit as claimed in claim 17, wherein the benzofuran derivative with antiarrhythmic activity is chosen from amiodarone, N,N-dibutyl-3-(4-((2-butyl-5-methylsulfonamido)benzofuran-3-ylcarbonyl)phenoxy] propylamine or one of the salts thereof, N-desethylamiodarone and N-butyl-3-[4-((2-butyl-5-methylsulfonamido)benzofuran-3-ylcarbonyl)phenoxy] propylamine.

20. The kit as claimed in claim 17, wherein the angiotensin II antagonist is irbesartan and the benzofuran derivative with antiarrhythmic activity is amiodarone.

21. The method as claimed in claim 1, comprising administering an angiotensin II antagonist which is irbesartan and a benzofuran derivative with antiarrhythmic activity which is amiodarone.

22. The method as claimed in claim 1, comprising administering synergistically effective amounts of the angiotensin II antagonist and the benzofuran derivative with antiarrhythmic activity.

23. The pharmaceutical composition as claimed in claim 5, wherein the angiotensin II antagonist and the benzofuran derivative with antiarrhythmic activity are present in synergistically effective amounts.

* * * * *